US006251945B1

United States Patent
Einig et al.

(10) Patent No.: US 6,251,945 B1
(45) Date of Patent: Jun. 26, 2001

(54) PHARMACEUTICAL MIXTURE COMPRISING A COMBINATION OF A PROFEN AND OTHER ACTIVE COMPOUNDS

(75) Inventors: Heinz Einig, Neustadt; Harald Hach, Birkweiler, both of (DE); Raymond Eason, Shreveport, LA (US); Bernd W. Müller, Flintbek (DE); Richard C. Thompson, Shreveport, LA (US)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/245,112

(22) Filed: Jan. 14, 1999

(51) Int. Cl.$^7$ .............................. A01N 37/10; A61K 31/19
(52) U.S. Cl. ................................................. 514/570
(58) Field of Search ............................................. 514/570

(56) References Cited

U.S. PATENT DOCUMENTS 5,631,296   5/1997   Birrenbach et al. ................. 514/570

FOREIGN PATENT DOCUMENTS

| 607467 | 7/1994 | (EP) . |
| 456720 | 6/1995 | (EP) . |
| 89/02266 | 3/1989 | (WO) . |

OTHER PUBLICATIONS

Abstract to JP 09157162 A, 1997, Aug. 1997.*
Efentakis, M. et al., "Influence of surfactants on Drug Release from a hydrophobic matrix", Abstract to International Journal of Pharmaceutics, (Netherlands), Mar. 31, 1991, vol. 70, pp. 153–158.*
Murray et al., *Pharm. Ind.*, 1998, pp. 257–262.

* cited by examiner

*Primary Examiner*—Dwayne C. Jones
(74) *Attorney, Agent, or Firm*—Keil & Weinkauf

(57) ABSTRACT

A pharmaceutical mixture comprising a profen and one or more additional active compounds is described which has a total active compound content of over 85% and contains up to 1%, based on the content of the profen, of a nonionic surfactant having an HLB of ≧9 and a customary disintegrant and a lubricant.

10 Claims, No Drawings

PHARMACEUTICAL MIXTURE COMPRISING A COMBINATION OF A PROFEN AND OTHER ACTIVE COMPOUNDS

BACKGROUND OF THE INVENTION

The present invention relates to a pharmaceutical mixture comprising a combination of a profen and other active compounds.

In the development of pharmaceutical forms, in particular in the case of profen-containing active compound combinations, the object is generally to find an optimum between 3 opposing objectives:

1. Both from the point of view of the pharmaceutical manufacturer and of the patient, it should be possible to prepare a pharmaceutical form as economically as possible. In the case of tablets, this means that with a fixed dose of active compound which is prespecified out of therapeutic necessity, the amount of the other auxiliaries which are added to the tablets should be kept as low as possible. The lower the amount of auxiliaries, the lower the production costs, which can likewise have an effect on the sale price. The production of tablets should also be as simple as possible and only comprise a few working steps in order likewise to be able to save costs in this way.
2. A tablet should optimally make available the active compound contained therein to the patient. This means an instant-release tablet should disintegrate very rapidly in the digestive fluids and rapidly release the active compound.
3. In order that it is easy to swallow, the tablet should have as small a form as possible (this applies particularly to high-dose active compounds). Small pharmaceutical forms are better accepted by patients and markedly increase so-called patient compliance.

It is almost impossible to fulfill these 3 requirements at the same time. When processing active compounds which are not extremely highly soluble, rapid release of an active compound from a tablet is achieved only by the addition of relatively large amounts of solubilizing auxiliaries and relatively large amounts of substances which bring about rapid disintegration and thus also rapid dissolution of the tablets. If the active compound can moreover only be tableted with difficulty, the production of a tablet is only possible using additional auxiliaries which compensate for the disadvantages of the poor tabletability. Moreover, in the production of ready-to-press tableting materials, in very many cases a laborious granulation step is also necessary beforehand. It is therefore usually impossible to develop a small and economical form.

All these disadvantages apply in particular to combinations of profens and other pharmaceuticals.

A further disadvantageous aspect of the profen monopreparations is that the profens contained therein do not dissolve well. Problems can therefore occur with respect to bioavailability. Therefore, for ibuprofen US Pharmacopeia USP XXIII, for example, requires a profen dissolution rate of at least 80% of the active compound after 60 minutes in order to ensures good bioavailability.

The profen ibuprofen, for example, further shows very poor tableting behavior. The added auxiliaries must therefore at the same time also compensate for this disadvantage. A check of most tablets available on the market which only contain ibuprofen shows that the amount of active compound in the total weight of the tablets as a rule is only 55–65%.

It is further common to all these tablets that, for the preparation of the compressable tableting material, a conventional granulation or compaction must be added, since otherwise adequate solidity cannot be achieved during tableting. Granulation, however, is expensive and time-consuming.

A further criterion of the quality of profen-containing tablets is the release of the active compound in vitro. Thus, according to Sucker, Fuchs and Speiser in: Pharmazeutische Technologie [Pharmaceutical Technology], Georg Thieme Verlag Stuttgart, 1978, page 283, the dissolution rate of poorly soluble substances can be increased in many cases by the addition of solubilizers. However, if it is attempted to increase the dissolution rate, for example, of ibuprofen by the addition of a solubilizer of the polyethylene glycol type, only minor success is achieved. The same applies if the solubilizer is replaced by a ionic surfactant such as sodium dodecylsulfate.

These abovementioned stipulations are additionally made difficult if profens are combined with one or other active compounds, which very often occurs in pharmaceutical practice. In this case, to the poor pharmaceutical processing properties of profens are added those of other active compounds.

Thus, for example, the combination of 200 mg of ibuprofen with 60 mg of pseudoephedrine hydrochloride, a nasal decongestant, has the problem that both active compounds are poorly tabletable. The poor tabletability of pseudoephedrine hydrochloride can be confirmed in that, with this active compound, the tablet in the so-called direct tableting process can only be prepared with up to at most 35% contents by weight of pseudoephedrine hydrochloride. If, in the case of pseudoephedrine hydrochloride, concentrations higher than 35% are desired, a more complicated and more expensive granulation step has to be performed before the tableting. Thus, the concentration of the two active compounds in a tablet can only be increased to 68% by a complicated granulation of ibuprofen and pseudoephedrine hydrochloride with further pharmaceutical auxiliaries, as demonstrated in Comparison Example 5. In this case, however, the release of ibuprofen is considerably worsened.

Some combination preparations of profens, in particular of ibuprofen, with other active compounds are already on the market, i.e. with pseudoephedrine hydrochloride, caffeine and, recently, a combination of 200 mg of ibuprofen and 7.5 mg of hydrocodone bitartrate. The tablet weight of this combination is 400 mg.

All these combination preparations have an active compound content, based on the tablet weight, of approximately 50–60%. This means that the tablets are all very large and are difficult to swallow.

BRIEF SUMMARY OF THE INVENTION

Surprisingly it has now been found that profens in combination with additional active compounds which can have a very high content in the total weight, can be processed very simply to give tablets which meet the very high pharmaceutical demands. These tablets are small and easy to swallow and exhibit a very rapid onset of action.

DETAILED DESCRIPTION OF THE INVENTION

The invention relates to a pharmaceutical mixture containing a profen and one or more other active compounds, which has a total active compound content of over 85%, preferably over 90%, and contains up to 1% of a nonionic surfactant having an HLB of $\geq 9$ and a customary disintegrant and a lubricant and, if appropriate, celluloses and/or hydroxyalkylcelluloses.

HLB is understood as meaning the "hydrophiliclipophilic balance", cf. Sucker, Fuchs and Speiser in: Pharmazeutische Technologie [Pharmaceutical Techology], Georg Thieme Verlag Stuttgart, 1978, page 305. The HLB in the mixture according to the invention is ≧9, preferably ≧11 and in particular ≧12.

The details in percent (%) relate to percentage by weight everywhere in the application.

The designation "Trofen" means antiinflammatory substances containing the structural element

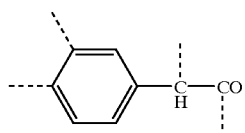

in which the dashed lines represent free valences.

Examples of such compounds are preferably ibuprofen and its optically active S form. Further suitable profens are flunoxaprofen, flurbiprofen, ibufenac, ibuproxam, ketoprofen and loxoprofen. The compounds can optionally be present in the form of their physiologically tolerable salts. These are to be understood as meaning the alkali metal and alkaline earth metal salts and salts with amino acids such as lysine. Preferred salts are the sodium salt and the lysinate.

Other active compounds in the mixture which may be mentioned by way of example are pseudoephedrine, ephedrine, phenylpropanolamine, tripolidine, acetylcystire, ambroxol, azelaic acid, dihydrocodeine, hydrocodone and caffeine.

The amount of other active compound in the mixture is in the range from approximately 0.5 to 70% of the amount of profen. It is dependent on the strength of the active compound to which the profen is added, and on the strength of the effect which it is wished to achieve with the additional active compound.

The term "pharmaceutical mixture" particularly includes administration forms such as tablets, film-coated tablets, sugar-coated tablets and the mixtures and pellets which are filled into the hard gelatin capsules.

The high active compound content in the administration form is achieved by incorporating into the administration form an amount of up to 1%, preferably 0.01–0.8%, (based on the amount of profen in the administration form) of a nonionic surfactant. Larger amounts of surfactant do not produce any further advantages.

Suitable nonionic surfactants having an HLB of 9 and over are, for example, sucrose esters; partial fatty acid esters of polyhydroxyethylenesorbitan, such as polyethylene glycol(20) sorbitan monolaurate, monopalmitate, monostearate and monooleate; polyethylene glycol(20) sorbitan tristearate and trioleate (which are obtainable, for example, under the trade name Tween®; polyethylene glycol(4) sorbitan monolaurate and monostearate; polyethylene glycol(5) sorbitan monooleate, polyhydroxyethylene fatty alcohol ethers such as polyoxyethylene cetyl stearyl ether (which are obtainable, for example, under the trade name Cremophor® O); corresponding lauryl ethers (which are obtainable, for example, under the trade names Brij® 30 and Brij® 35); polyhydroxyethylene fatty acid esters (which are obtainable, for example, under the trademarks Myrj® 45, Myrj® 52 and Myrj® 59); ethylene oxide/propylene oxide block copolymers (which are obtainable, for example, under the trade names Pluronic® and Lutrol®); furthermore sugar ethers and sugar esters; phospholipids and their derivatives; and ethoxylated triglycerides such as the derivatives of castor oil (which are obtainable, for example, under the trade names Cremophor® EL, Cremophor® RH, Cremophor® RH 40, Cremophor® RH 60). Among these, Cremophor® RH 40 and Cremophor® RH 60 are particularly suitable. The surfactants obtainable under the designation Tween® likewise behave very favorably. Very particular mention is to be made of Tween® 80. The use of mixtures of these surfactants is likewise advantageous.

Customary disintegrants are, for example, sodium carboxymethyl starch and sodium carboxymethylcellulose. Coarse-grain celluloses have the same properties.

The amount of disintegrant in the pharmaceutical form is normally in the range from 1 to 4%.

Suitable lubricants are, for example, magnesium stearate and calcium stearate, stearic acid, stearic acid derivatives (which are obtainable, for example, under the trade names Precirol®), talc, Aerosil®, polyethylene glycols (mainly types having a molecular weight of 4000 and higher) and hydrogenated cottonseed and castor oils.

The amount of lubricant in the pharmaceutical form is normally in the range from 0.1 to 0.7%.

The addition of celluloses or hydroxyalkylcelluloses to the pharmaceutical form is not absolutely necessary, but the addition of a small amount of such a substance proves advantageous. The addition of hydroxyalkylcelluloses, in particular of hydroxymethylpropylcellulose 3 cp, hydroxymethylpropylcellulose 6 cp or hydroxypropylcellulose such as, for example, Klucel® EF, is preferred.

The amount of celluloses and hydroxyalkylcelluloses in the pharmaceutical form is normally in the range from 1 to 4%.

Although other pharmaceutical auxiliaries can be added to the pharmaceutical forms, they are not necessary for their production.

The mean particle size of the profen used does not play any great part in the preparation of the administration forms, as a rule it is 10–100 μm, preferably 20–80 μm.

The novel mixture is especially suitable for the production of solid pharmaceutical forms such as granules in hard gelatin capsules or tablets which contain the active compounds in an amount from 85–98%, preferably 90–98%, of their total weight.

The expression "pharmaceutical form" should distinguish not only the so-called "finished pharmaceutical form", but also tablets without a coating or, in the case of multilayer tablets, the layer containing the active compounds or the granules containing the active compounds, which can be shaped to give pellets.

Tablet coatings are not considered in the calculation of the % content of the pharmaceutical form. If the tablets are press-coated or multilayer tablets, the % details for the active compounds and the auxiliaries thus relate only to the portions or layers of the pharmaceutical form which contain the active compounds.

For the preparation of, for example, tablets, the surfactants are preferably mixed in dry form with the active compound mixture, that is, in the case of a liquid surfactant, the addition and dispersion of the surfactant is carried out without further addition of a diluent and, in the case of a solid surfactant, in some cases without prior micronization.

The surfactants, however, can also be dissolved in water or organic solvents and evenly distributed on the active compounds. However, the moist mixture then still has to be dried. The amount of water or solvent used here is 3–10% (based on the total amount), clearly below the amount of liquid which is needed for granulation (approximately 35–40%, based on the total amount).

In some cases, it is adequate if the profen is treated with the surfactants on its own without the additional other active compound. As a rule, however, it is more favorable to treat all active compounds of the combination preparation at the same time with the nonionic surfactants employed.

After addition of the customary auxiliaries, the mixture thus obtained can be compressed directly, that is without granulation, to give tablets.

It was extremely surprising that as a result of the addition of the surfactants mentioned, which, for example, in the case of the polyoxyethylene sorbitan esters are usually highly viscous liquids having a honey-like consistency, profens such as ibuprofen in combination with other active compounds can be processed simply to give tablets having very high pharmaceutical demands. It contradicts all previous experiences that as a result of the addition of a surfactant to a poorly tabletable active compound such as ibuprofen a good compressibility can be achieved. The previous experiences assume that compressibility more likely decreases as a result of the addition of surfactants.

Furthermore, it is surprising that in most cases not only is the dissolution rate of the profen markedly increased compared with conventional formulations, but that this is also the case for the other active compounds added to the combination.

Moreover, it is very surprising that the novel tablets even have a very high hardness when they are pressed using an only relatively low compression force.

Further extremely surprising is the good flow behavior of these mixtures, which is markedly better than when the mixture is not treated with a nonionic surfactant. Moreover, the mixtures treated with a nonionic surfactant are not prone to demixing.

The following examples illustrate the invention.

If not stated otherwise, all measurements of active compound releases were carried out according to USP XXIII.

EXAMPLE 1

2 kg of ibuprofen and 600 g of pseudoephedrine hydrochloride were mixed with one another. 10 g of Cremophor® RH 40 were then intermixed and stirring was continued for a further 10 min. After this, 100 g of Avicel® PH 102, 5 g of Aerosil® 200, 5 g of magnesium stearate and 50 g of Primojel® were added and the mixture was pressed to give tablets having a weight of 277 mg in a circular and lenticular die of 9 mm. At a press force of 5 kN, tablets having a hardness of 70–80 N were obtained. The friability was under 0.4% (Roche Friabilator 400 rpm). In water, these tablets disintegrate within 40 seconds and release the active compound ibuprofen to 100% after 5 minutes according to the USP XXIII method. The release of pseudoephedrine hydrochloride was carried out in a separate experiment likewise according to USP XXIII (paddle apparatus, 900 ml of water, 50 rpm). Here too, 100% of the active compound was dissolved after 5 minutes.

Some of the tablets obtained above were coated with a film coating of the following composition:

| | |
|---|---|
| Polydextrose | 28% |
| Hydroxymethylpropylcellulose 2910 3 cp | 30% |
| Hydroxymethylpropylcellulose 2910 15 cp | 10% |
| Polyethylene glycol 400 | 6% |

-continued

| | |
|---|---|
| Titanium dioxide | 18% |
| Iron oxide | 8% |

1 part by weight of this mixture was processed with 4 parts by weight of a mixture of deionized water and ethanol (1:1) with intensive stirring to give a suspension. The tablets were coated with this suspension in a laboratory coater. The weight of the film coating per tablet was 15 mg.

The disintegration time of these film-coated tablets in water was 1 min, after 5 min both the ibuprofen and the pseudoephedrine hydrochloride were dissolved to 100%.

EXAMPLE 2

2 kg of ibuprofen and 10 g of Cremophor® RH 40 were mixed with one another and stirred for approximately 10 min. 631 g of pseudoephedrine DTP (pseudoephedrine hydrochloride with addition of 5% hydroxypropylmethylcellulose, manufacturer: Knoll AG, D-67008 Ludwigshafen), 70 g of Avicel® PH 102, 5 g Aerosil® 200, 5 g of magnesium stearate and 50 g of Primojel® were then added and the mixture was pressed to give tablets having a weight of 278 mg in a circular and lenticular die of 9 mm diameter. At a press force of 5 kN, tablets having a hardness of 100–120 N were obtained. The friability was under 0.3% (Roche Friabilator 400 rpm). In water, these tablets disintegrated within 30 sec and released the active compound ibuprofen to 100% after 5 min according to USP XXIII method. The release of pseudoephedrine hydrochloride was also carried out in a separate experiment according to USP XXIII. Here too, 100% of the active compound was dissolved after 5 min.

EXAMPLE 3

200 g of ibuprofen were mixed with 0.5 g of Myrj® 59 and 50 g of caffeine, 1 g of Aerosil® 200, 1 g of magnesium stearate, 5 g of Avicel® PH 102 and 12.5 g of AcDiSol® and the mixture was then pressed in an eccentric press having a 10 mm lenticular die at a press force of 6 kN to give tablets having a weight of 270 mg and a hardness of 120 N. The tablets disintegrated within 1 min in water and had a low friability of 0.6%. After 5 min, both ibuprofen (according to USP XXIII) and caffeine were dissolved to 85%. The release of caffeine was measured analogously to the procedure indicated in USP XXXII for acetaminophen and caffeine tablets.

EXAMPLE 4

256 g of sodium ibuprofenate dihydrate were mixed with 1 q of Myrj® 59, 50 g of caffeine, 1 g of Aerosil® 200, 1 g of magnesium stearate, 5 g of Avicelz PH 102 and 12.5 g of AcDiSol® were added and the mixture was then pressed in an eccentric press having a 10 mm lenticular die at a press force of 6 kN to give tablets having a weight of 326 mg and a hardness of 130 N. The tablets disintegrated within 1 min in water, had a low friability of 0.6% and released ibuprofen within 5 min according to USP XXIII and caffeine likewise quantitatively within 5 minutes. The release of caffeine was carried out as in Example 3.

EXAMPLE 5

256 g of sodium ibuprofenate dihydrate and 10 g of dihydrocodeine hydrogentartrate were mixed with 0.8 g of Myrj®59. 1 g of Aerosil® 200, 1 g of magnesium stearate, 5 g of Avicel® PH 102 and 12.2 g of AcDiSol® were then added. The mixture was then pressed in an eccentric press having a 10 mm lenticular die at a press force of 4 kN to give tablets having a weight of 286 mg of hardness 90 N. The tablets disintegrated within 30 sec in water, had a low friability of 0.49% and released ibuprofen within 3 min according to USP XXIII and dihydrocodeine hydrogentartrate quantitatively into solution within 5 min.

The release of dihydrocodeine hydrogentartrate from the tablets was carried out as follows:

The dissolution model employed was a paddle apparatus according to USP XXIII with 900 ml of 0.1 N hydrochloric acid at 50 rpm and 37° C. After 5 minutes, 50 ml were taken as a measurement sample and filtered through a 0.45 μm filter. The comparison used was a measuring solution of 0.556 mg of dihydrocodeine hydrogentarcrate in 50 ml of 0.1 N hydrochloric acid. The measurements on the test solution and the comparison solution were carried out in a spectrophotometer with a 5 cm cuvette at the wavelength 260–300 nm. The analysis was carried out according to the 1st derivative of the absorption spectrum with MCA curve fitting/maximum according to Likelihood.

EXAMPLE 6

Example 5 was repeated, but instead of the hydrocodeine salt the same amount of hydrocodone hydrogentartrate was employed. The results were virtually identical.

COMPARISON EXAMPLES

Comparison Example 1

Analogously to Example 1, it was attempted to prepare tablets in which, however, no surfactant was incorporated. Only at a press force of over 29 kN could tablets having a hardness of 20 N be obtained, which had a high friability of over 20%, a disintegration time of 5 min and an active compound release of 15% of ibuprofen after 5 min. Because of the high friability and the extremely high press force, such tablets, however, cannot be used in practice.

Comparison Example 2

This comparison example shows the positive effect of the nonionic surfactants:

Example 2 was repeated, but without addition of the surfactant Cremophor® RH40. All other constituents were mixed with one another and pressed to give tablets of 277 mg. Thus, by means of the pretreated pseudoephedrine DTP, hardnesses of 40–50 N at a press force of 17–18 kN can indeed be obtained. These tablets disintegrated, however, after only 10 min and released ibuprofen only to 10% after 5 min and to 55% after 30 min.

Comparison Example 3

Direct tableting of iburofen/pseudoephedrine hydrochloride

| Composition per tablet: | | |
|---|---|---|
| a. Ibuprofen | 200 mg | 42.1% content/tablet |
| b. Pseudoephedrine HCl | 60 mg | 12.6% content/tablet |
| c. Avicel® PH 102 | 133 mg | |
| d. Pharmacoat® 603 | 39 mg | |
| e. Magnesium stearate | 3 mg | |
| f. AcDiSol® | 37 mg | |
| g. Aerosil® 200 | 3 mg | |

All constituents were mixed in a batch size of 3 kg and pressed to give tablets of 475 mg in 11 mm dies. The following physical data on the tablets were obtained:

| | | Hardness (N) | Decomposition (min) | Friability (%) | Release of 90% of ibuprofen |
|---|---|---|---|---|---|
| Press force | 2.9 kN | 24 | 1.0 | 10 | 15 (min) |
| Press force | 6.4 kN | 59.7 | 3.5 | 0.6 | 25 (min) |
| Press force | 32.2 kN | 86.8 | 9.0 | 0.9 | 30 (min) |

Higher concentrations of the active compounds did not lead to acceptable tableting results. By far the best results were to be obtained using the abovementioned Avicel® PH 102. Starch or lactose instead of Avicel® had an adverse effect on the results.

Comparison Example 4

Compaction of ibuprofen/pseudoephedrine hydrochloride

| Composition per tablet: | | |
|---|---|---|
| a. Ibuprofen | 200 mg | 42.1% content/tablet |
| b. Pseudoephedrine HCl | 60 mg | 12.6% content/tablet |
| c. Pharmacoat® 603 | 20 mg | |
| d. Lactose | 50 mg | |
| e. Corn starch | 50 mg | |
| f. Magnesium stearate | 1 mg | |

The mixture was compacted in a batch size of 3 kg on a laboratory compactor. The material pressed in this way (flakes) was first comminuted on a Frewitt machine using a 4 mm screen and then using a 1.2 mm screen.

The following auxiliaries were then admixed per tablet:

| | |
|---|---|
| g. Avicel® PH 102 | 46 mg |
| h. Pharmacoat® 603 | 19 mg |
| i. AcDiSol® | 25 mg |
| j. Aerosil® 200 | 2 mg |
| k. Magnesium stearate | 2 mg | and tablets of 475 mg weight were pressed in 11 mm dies. The results can be seen from the following table:

|  | | Hardness (N) | Decomposition (min) | Friability (%) | Release of 90% of ibuprofen |
|---|---|---|---|---|---|
| Press force | 4.5 kN | 75 | 15.5 | 0.3 | 30 (min) |
| Press force | 7.8 kN | 88 | 19.5 | 0.2 | 35 (min) |
| Press force | 33.9 kN | 105 | 28.0 | 0.3 | 45 (min) |

Compared with direct tableting, greater hardnesses can be achieved which, however, were accompanied by the poorer disintegration time and lower active compound release of ibuprofen.

Comparison Example 5

Moist granulation of ibuprofen/pseudoephedrine hydrochloride

In the case of moist granulation, it was possible according to the following recipe to increase the contents of the active compounds with reduced tablet weight.

| Recipe per tablet | | |
|---|---|---|
| a. Ibuprofen | 200 mg | 52.5% content/tablet |
| b. Pseudoephedrine HCl | 60 mg | 15.8% content/tablet |
| c. Avicel ® PH 101 | 40 mg | |
| d. Pharmacoat ® 603 | 24 mg | |
| e. Avicel ® PH 102 | 28 mg | |
| f. AcDiSol ® | 24 mg | |
| g. Magnesium stearate | 2 mg | |
| h. Aerosil ® 200 | 2 mg | |

In a total batch of 3 kg, the substances a–d were mixed with one another and granulated with water. After moist screening through a 3 mm screen and drying in a recirculating air oven at 45° C., the mixture was again screened through a 1 mm screen and the substances e–h were admixed. Tablets having a weight of 380 mm were pressed.

|  | | Hardness (N) | Decomposition (min) | Friability (%) | Release of 90% of ibuprofen |
|---|---|---|---|---|---|
| Press force | 4.1 kN | 69 | 15 | 0.2 | 25 (min) |
| Press force | 9.4 kN | 114 | 25 | 0.2 | 40 (min) |
| Press force | 33.9 kN | 100 | 25 | 0.2 | 45 (min) |

Moist granulation did lead to higher active compound concentrations in the tablet, but was accompanied by a lower release of the active compound ibuprofen than in Comparison Examples 3 and 5.

What is claimed is:

1. A solid pharmaceutical mixture comprising a profen and one or more additional active compounds, which has a total active compound content of over 85% and contains up to 1%, based on the content of the profen, of a nonionic surfactant having an HLB of $\geq 9$ and a customary disintegrant and a lubricant.

2. A pharmaceutical mixture as claimed in claim 1, wherein the surfactant employed has an HLB of $\geq 11$.

3. A pharmaceutical mixture as claimed in claim 1, wherein the surfactant employed has an HLB of $\geq 12$.

4. A pharmaceutical mixture as claimed in claim 1, wherein the mixture is a tablet.

5. A pharmaceutical mixture as claimed in claim 1, having an active compound content of $\geq 80\%$.

6. A pharmaceutical mixture as claimed in claim 1, which has an in-vitro release of the active compound of $\geq 80\%$ after 5 minutes.

7. A pharmaceutical mixture as claimed in claim 6, which has an in-vitro release of the active compound of $\geq 90\%$ after 5 minutes.

8. A pharmaceutical mixture as claimed in claim 1, wherein the profen contained is ibuprofen.

9. A pharmaceutical mixture as claimed in claim 1, wherein the profen contained is flurbiprofen.

10. A pharmaceutical mixture according to claims 1, which contains the additional active compound(s) in an amount of from approximately 0.5 to 70%, based on the profen employed.

* * * * *